United States Patent
Falkenstein et al.

(10) Patent No.: US 11,891,430 B2
(45) Date of Patent: Feb. 6, 2024

(54) MULTISTEP FINAL FILTRATION

(71) Applicant: Hoffmann-La Roche Inc., Little Falls, NJ (US)

(72) Inventors: Roberto Falkenstein, Munich (DE); Klaus Schwendner, Weilheim (DE)

(73) Assignee: Hoffmann-La Roche Inc., Little Falls, NJ (US)

( * ) Notice: Subject to any disclaimer, the term of this patent is extended or adjusted under 35 U.S.C. 154(b) by 935 days.

(21) Appl. No.: 16/660,635

(22) Filed: Oct. 22, 2019

(65) Prior Publication Data
US 2020/0291097 A1   Sep. 17, 2020

Related U.S. Application Data

(63) Continuation of application No. 15/444,018, filed on Feb. 27, 2017, now abandoned, which is a continuation of application No. 13/394,766, filed as application No. PCT/EP2010/064487 on Sep. 29, 2010, now abandoned.

(30) Foreign Application Priority Data

Oct. 1, 2009   (EP) .................................. 09012460

(51) Int. Cl.
| | | |
|---|---|---|
| C07K 16/06 | (2006.01) | |
| C07K 16/28 | (2006.01) | |
| C07K 16/32 | (2006.01) | |
| C07K 1/16 | (2006.01) | |
| C07K 1/34 | (2006.01) | |
| C07K 1/36 | (2006.01) | |

(52) U.S. Cl.
CPC ........ *C07K 16/065* (2013.01); *C07K 16/2866* (2013.01); *C07K 16/32* (2013.01)

(58) Field of Classification Search
None
See application file for complete search history.

(56) References Cited

U.S. PATENT DOCUMENTS

| | | | |
|---|---|---|---|
| 4,592,848 A | 6/1986 | Pabst | |
| 6,127,526 A | 10/2000 | Blank et al. | |
| 8,198,407 B1* | 6/2012 | Burton | .................. C07K 14/745 |
| | | | 435/69.6 |
| 2002/0090662 A1* | 7/2002 | Ralph | .............. G01N 33/57415 |
| | | | 435/7.92 |
| 2003/0153735 A1 | 8/2003 | Breece et al. | |
| 2006/0034850 A1 | 2/2006 | Weidanz et al. | |
| 2006/0051347 A1 | 3/2006 | Winter et al. | |
| 2006/0185025 A1 | 8/2006 | Oshimura et al. | |
| 2007/0087017 A1* | 4/2007 | Olivieri | .................. B01D 61/16 |
| | | | 424/250.1 |
| 2008/0247949 A1 | 10/2008 | Fujibashi et al. | |
| 2008/0248047 A1 | 10/2008 | Das et al. | |
| 2010/0145022 A1 | 6/2010 | Romero et al. | |
| 2015/0274773 A1* | 10/2015 | Becker | .................. C12M 47/12 |
| | | | 530/414 |

FOREIGN PATENT DOCUMENTS

| | | |
|---|---|---|
| CS | 247484 | 4/1985 |
| EP | 1 923 072 A1 | 9/2006 |
| EP | 1 614 693 A1 | 11/2006 |
| WO | 03/066662 A2 | 8/2003 |
| WO | 03/066662 A3 | 8/2003 |
| WO | WO-2004001007 A2 * | 12/2003 ....... A61K 39/39591 |
| WO | 2006/072564 A1 | 7/2006 |
| WO | 2009/010269 A1 | 1/2009 |
| WO | 2009/010271 | 1/2009 |
| WO | 2009/010271 A2 | 1/2009 |
| WO | 2009/010271 A3 | 1/2009 |
| WO | 2009/058769 A1 | 5/2009 |
| WO | 2010/056550 A1 | 5/2010 |

OTHER PUBLICATIONS

Zhou et al. "Implementation of advance technologies in commercial monoclonal antibody production" Biotechno. J. 2008, 3, 1185-1200 (Year: 2008).*
Jul. 28, 2014 (Jul. 8, 2014), XP055131833, Retrieved from the Internet: URL:https//web.archive.org/web/20090424091259/http://www.cdc.gov/nchs/data/nhanes/nhanes_01_2/106_b_met_ferritin.pdf [retrieved on Jul. 28, 2014] (2014).
Aldington et al., "Scale-up of monoclonal antibody purification processes" J Chromatogr B 848(1):64-78 (Mar. 12, 2007).
Anonymous: 'Laboratory Procedure Manual', Jan. 1, 2004, XP055131817, Retrieved form the Internet: URL: http://www.cdc.gov/nchs/data/nhanes/nhanes_01_02/106_b_met_ferritin.pdf [retrieved on Jul. 28, 2014]; & Anonymous: 'waybackmachine for http://www.cdc.gov./nchs/data/nhanes/nhanes_01-02/106_b_met_ferritin.pdf' (2004).
Honig et al., "Impact of Design and Selection of Prefilters on Operating Cost" Filtration and Separation 34(1):73-78 (Jan. 1, 1997).
Hood et al. Immunology Benjamin, 2nd edition, New York:The Benjamin/Cummings Publishing Co., Inc., (1984).
International Search Report and Written Opinion for International Patent Application No. PCT/EP2010/064487.
Merrick and Hawlitschek, "A complete system for quantitative analysis of total DNA, protein impurities and relevant proteins" Biotech Forum Europe 9:398-403 ( 1992).
Palecek et al., "Intermolecular Electrostatic Interactions and Their Effect on Flux and Protein Deposition during Protein Filtration" Biotechnol. Prog. 10:207-213 ( 1994).

(Continued)

*Primary Examiner* — Daniel E Kolker
*Assistant Examiner* — James L Rogers
(74) *Attorney, Agent, or Firm* — Charles Wong (57) ABSTRACT

Herein is reported a method for the final filtration of concentrated polypeptide solutions comprising the combination of two immediately consecutive filtration steps with a first filter of 3.0 μm and 0.8 μm pore size and a second filter of 0.45 μm and 0.22 μm pore size.

16 Claims, 8 Drawing Sheets

(56) References Cited

OTHER PUBLICATIONS

Shukla et al., "Host cell protein clearance during protein A chromatography: development of an improved column wash step" Biotechnol. Prog 24:1115-1121 (Oct. 14, 2008).
English translation of relevant paragraphs of CGK1 to CGK5 cited in the Reexamination Notification in the corresponding Chinese Patent Appication No. 201510004012.6, dated Sep. 3, 2020.
English-language version of the search report or official action dated Sep. 3, 2020, in the corresponding Chinese Patent Application No. 201510004012.6.
Huang et al. (CGKI: Microporous Membrane and Application Thereof, Ce Huang et al., as 1980 editor-in-chief, published by Shanghai Science and Technology Literature Press, pp. 182-183.).
Kang (CGK4: Liquid Filtration and Filter Media, Yong Kang et al. as editor-in-chief, published by Chemical Industry Press, p. 193. with English translation of the abstract), 2008.
Wu (CGK3: Guidelines for Key Technologies of Pharmaceutical Engineering, Junke Wu as editor-in-chief, Published by the Fourth Military Medical University Press, pp. 280-281.), 2008.
Xue et al. (CGK5: Principles of Chemical Engineering 2006 vol. 2, edited by Xue Xue, published by Hunan Science and Technology Press, pp. 179-180.).
Zhou, J. et al. CGK2: Pharmacy (CGK2: Pharmacy, Jianping Zhou as editor-in-chief, published by Southeast University Press, p. 364.), 2007.

\* cited by examiner

MULTISTEP FINAL FILTRATION

RELATED APPLICATIONS

This application is a Continuation application of U.S. application Ser. No. 15/444,018, filed Feb. 27, 2017, which is a Continuation application of U.S. application Ser. No. 13/394,766, filed Mar. 7, 2012, which is a US national phase application of PCT/EP2010/064487, filed Sep. 29, 2010, which claims benefit of priority to EP Application No. 09012460.3 filed Oct. 1, 2009, each of which are incorporated herein by reference in its entirety.

FIELD OF THE INVENTION

Provided herein are methods for the final filtration of concentrated polypeptide solutions comprising the combination of two immediately consecutive filtration steps with a first filtration step with a pre-filtration with a filter with a pore size of 3.0 μm and a main-filtration with a filter with a pore size of 0.8 μm and a second filtration with a pre-filtration with a filter with a pore size of 0.45 μm and with a main-filtration with a filter with a pore size of 0.22 μm.

BACKGROUND OF THE INVENTION

Protein solutions with a concentration of more than 100 g/l are prone to difficulties during the final filtration step, e.g. by having only low transmembrane fluxes or blocking of the employed filter by aggregates or particles formed during the formulation or concentration process or due to added excipients resulting in an increased viscosity of the concentrated solution.

The combination of high viscosity and increased particle or aggregate content results often in the blocking of the pores of an employed 0.22 μm final filtration filter. As a consequence either the filter has to be replaced during the filtration step, i.e. before the batch is completely processed, or an increased filter surface has to be used.

Further it has been observed that a combination of a filter with a pore size of 0.45 μm and a filter with a pore size of 0.22 μm has no advantages, e.g. provided as Sartobran P 0.45/0.22 μm filter. Filter with an increased pore size probable to circumvent the before described problems are employed as depth-filters or pre-filters but not a final filters.

In DE 4 204 444 a combination of a 1.2 μm pre-filter to remove water droplets from a gas stream prior to a 0.2 μm sterile-filtration is reported. A filter unit comprising two filters of different pore size, whereby the filter of the smaller pore size is flexible allowing by changing the flow direction the filter to bend to reduce the resistance of the filter unit is reported in U.S. Pat. No. 4,488,961. In U.S. Pat. No. 5,643,566 a combination of a pre-filtration with a filter with a pore size of 0.45 μm and a sterile-filtration with a filter of a pore size of 0.22 μm is reported. A two-stage filter constructed using a membrane with a smooth interior underlaid with a thin, flexible porous membrane supported by a rigid screen support with a ridged expander tube is reported in EP 0 204 836. A combination of at least two membrane filter units of different membrane material and different filter pore size and filter pore geometries is reported in DE 3 818 860.

Aldington et al. (J. Chrom. B 848 (2007) 64-78) report a scale-up of monoclonal antibody purification processes. In CS 247484 a method of preparing immunoglobulin against human lymphocytes is reported.

SUMMARY OF THE INVENTION

It has been found that a combination of two filters each comprising a pre-filter and a main-filter and each with a specifically selected pore size can be used to filter highly concentrated immunoglobulin solutions during the final packaging step without the risk of pore blocking and the need to replace the filter during the filtration process.

One aspect as reported herein is a method for the preparation of an immunoglobulin solution comprising the following steps
   a) providing an immunoglobulin solution with a protein concentration of at least 100 g/l,
   b) filtering the immunoglobulin solution through a combination of a first and second filter, whereby the first filter comprises a pre-filter with a pore size of 3.0 μm and a main-filter with a pore size of 0.8 μm and the second filter comprises a pre-filter with a pore size of 0.45 μm and a main-filter with a pore size of 0.22 μm, and thereby preparing an immunoglobulin solution.

Another aspect as reported herein is the use of a filter combination as reported herein of a combination of a first and second filter, whereby the first filter comprises a pre-filter with a pore size of 3.0 μm and a main-filter with a pore size of 0.8 μm and the second filter comprises a pre-filter with a pore size of 0.45 μm and a main-filter with a pore size of 0.22 μm, for the final filtration of an immunoglobulin solution prior to active pharmaceutical ingredient preparation.

Another aspect as reported herein is a method for producing an immunoglobulin comprising the following steps
   a) providing a cell comprising a nucleic acid encoding the immunoglobulin,
   b) cultivating the cell,
   c) recovering the immunoglobulin from the cell or the cultivation medium,
   d) purifying the immunoglobulin with one or more chromatography steps and providing an immunoglobulin solution, and
   e) filtrating the immunoglobulin solution of step d) through a combination of a first and second filter, whereby the first filter comprises a pre-filter with a pore size of 3.0 μm and a main-filter with a pore size of 0.8 μm and the second filter comprises a pre-filter with a pore size of 0.45 μm and a main-filter with a pore size of 0.22 μm, and thereby producing an immunoglobulin.

A further aspect as reported herein is a kit comprising a first filter comprising a pre-filter with a pore size of 3.0 μm and a main-filter with a pore size of 0.8 μm and the second filter comprising a pre-filter with a pore size of 0.45 μm and a main-filter with a pore size of 0.22 μm.

In one embodiment the first filter has an area that is at most twice the area of the second filter. In another embodiment the first and second filter have about the same total filter area. In an embodiment the immunoglobulin solution comprises a sugar, and/or an amino acid, and/or a surfactant, and/or a salt. In a further embodiment the immunoglobulin solution has a concentration of from 100 g/l to 300 g/l. In still another embodiment the immunoglobulin solution has a volume of from 3 liter to 100 liter. In a further embodiment the filtrating is with an applied pressure of from 0.1 bar to 4.0 bar. In one embodiment the immunoglobulin solution has a concentration of 160 g/l or more and the filtrating is with an applied pressure of 1.45 bar or more. In a further embodiment of 1.50 bar or more. In another embodiment the immunoglobulin solution comprises a sugar and a surfactant and has a concentration of 125 mg/ml or more and the filtrating is with an applied pressure of 0.75 bar or less. In a further embodiment of 0.7 bar or less.

In one embodiment the immunoglobulin is an anti-IL13 receptor alpha antibody or an anti-HER2 antibody. In a further embodiment the purifying is with a protein A affinity chromatography step and at least one step selected from cation exchange chromatography, anion exchange chromatography, and hydrophobic interaction chromatography.

DETAILED DESCRIPTION OF THE INVENTION

It has been found that a combination of two filters or filter units each comprising a pre-filter and a main-filter and each with a specifically selected pore size can be used to filter highly concentrated and viscous, as well as formulated immunoglobulin solutions, i.e. comprising a sugar and a surfactant, during the final packaging step. Especially the combination of a first filter comprising a pre-filter an a main-filter with a pore size of 3.0 μm and 0.8 μm, respectively, and a second filter comprising a pre-filter and a main-filter with a pore size of 0.45 μm and 0.22 μm, respectively, is highly advantageous. With a single filter unit of this combination it has been possible to filtrate highly concentrated solutions containing in total e.g. 1 kg of an anti-IL-13Rα1 antibody or 6 kg of an anti-HER2 antibody and to package this amounts with only minor substance losses. In one embodiment a ratio of filer surface area to solution volume has been determined.

In one embodiment the immunoglobulin solution comprises the immunoglobulin and an excipient. In another embodiment the excipient comprises one or more substances selected from sugars, such as glucose, galactose, maltose, sucrose, trehalose and raffinose, amino acids, such as arginine, lysine, histidine, ornithine, isoleucine, leucine, alanine, glutamic acid, aspartic acid, glycine, and methionine, salts, such as sodium chloride, potassium chloride, sodium citrate, potassium citrate, sodium phosphate, potassium phosphate, and surfactants, such as polysorbates, and poly (oxyethylene-polyoxypropylene) polymers.

The filtrating as reported herein is used as the final filtration step in the production of a therapeutic antibody. It can be carried out after the required excipients, stabilizer and/or anti-oxidants have been added to the highly concentrated antibody solution. In one embodiment the ratio of amount of antibody in kg to total area of the filter is of from 1000 g/m$^2$ to 10,000 g/m$^2$. In another embodiment the ratio is of from 1000 g/m$^2$ to 6000 g/m$^2$. In still another embodiment the ratio is from 4000 g/m$^2$ to 6000 g/m$^2$.

A "polypeptide" is a polymer consisting of amino acids joined by peptide bonds, whether produced naturally or synthetically. Polypeptides of less than about 20 amino acid residues may be referred to as "peptides", whereas molecules consisting of two or more polypeptides or comprising one polypeptide of more than 100 amino acid residues may be referred to as "proteins". A polypeptide may also comprise non-amino acid components, such as carbohydrate groups, metal ions, or carboxylic acid esters. The non-amino acid components may be added by the cell, in which the polypeptide is expressed, and may vary with the type of cell. Polypeptides are defined herein in terms of their amino acid backbone structure or the nucleic acid encoding the same. Additions such as carbohydrate groups are generally not specified, but may be present nonetheless.

The term "immunoglobulin" refers to a protein consisting of one or more polypeptide(s) substantially encoded by immunoglobulin genes. The recognized immunoglobulin genes include the different constant region genes as well as the myriad immunoglobulin variable region genes. Immunoglobulins may exist in a variety of formats, including, for example, Fv, Fab, and F(ab)$_2$ as well as single chains (scFv) or diabodies.

The term "complete immunoglobulin" denotes an immunoglobulin which comprises two so called light immunoglobulin chain polypeptides (light chain) and two so called heavy immunoglobulin chain polypeptides (heavy chain). Each of the heavy and light immunoglobulin chain polypeptides of a complete immunoglobulin contains a variable domain (variable region) (generally the amino terminal portion of the polypeptide chain) comprising binding regions that are able to interact with an antigen. Each of the heavy and light immunoglobulin chain polypeptides of a complete immunoglobulin also comprises a constant region (generally the carboxyl terminal portion). The constant region of the heavy chain mediates the binding of the antibody i) to cells bearing a Fc gamma receptor (FcγR), such as phagocytic cells, or ii) to cells bearing the neonatal Fc receptor (FcRn) also known as Brambell receptor. It also mediates the binding to some factors including factors of the classical complement system such as component (C1q). The variable domain of an immunoglobulin's light or heavy chain in turn comprises different segments, i.e. four framework regions (FR) and three hypervariable regions (CDR).

The term "immunoglobulin fragment" denotes a polypeptide comprising at least one domain of the variable domain of a heavy chain, the $C_H1$ domain, the hinge-region, the $C_H2$ domain, the $C_H3$ domain, the $C_H4$ domain of a heavy chain, the variable domain of a light chain and/or the $C_L$ domain of a light chain. Also comprised are derivatives and variants thereof. For example, a variable domain, in which one or more amino acids or amino acid regions are deleted, may be present.

The term "immunoglobulin conjugate" denotes a polypeptide comprising at least one domain of an immunoglobulin heavy or light chain conjugated via a peptide bond to a further polypeptide. The further polypeptide is a non-immunoglobulin peptide, such as a hormone, or growth receptor, or antifusogenic peptide, or complement factor, or the like.

The term "filter" denotes both a microporous or macroporous filter. The filter comprises a filter membrane which itself is composed of a polymeric material such as, e.g. polyethylene, polypropylene, ethylene vinyl acetate copolymers, polytetrafluoroethylene, polycarbonate, poly vinyl chloride, polyamides (nylon, e.g. Zetapore™, $N_{66}$ Posidyne™), polyesters, cellulose acetate, regenerated cellulose, cellulose composites, polysulphones, polyethersulfones, polyarylsulphones, polyphenylsulphones, polyacrylonitrile, polyvinylidene fluoride, non-woven and woven fabrics (e.g. Tyvek®), fibrous material, or of inorganic material such as zeolithe, $SiO_2$, $Al_2O_3$, $TiO_2$, or hydroxyapatite. In one embodiment the filter membrane of the first and second filter is made of cellulose acetate.

For the purification of recombinantly produced immunoglobulins often a combination of different column chromatography steps is employed. Generally a protein A affinity chromatography is followed by one or two additional separation steps. The final purification step is a so called "polishing step" for the removal of trace impurities and contaminants like aggregated immunoglobulins, residual HCP (host cell protein), DNA (host cell nucleic acid), viruses, or endotoxins. For this polishing step often an anion exchange material in a flow-through mode is used.

Different methods are well established and widespread used for protein recovery and purification, such as affinity chromatography with microbial proteins (e.g. protein A or protein G affinity chromatography), ion exchange chromatography (e.g. cation exchange (carboxymethyl resins), anion exchange (amino ethyl resins) and mixed-mode exchange), thiophilic adsorption (e.g. with beta-mercaptoethanol and other SH ligands), hydrophobic interaction or aromatic adsorption chromatography (e.g. with phenyl-sepharose, aza-arenophilic resins, or m-aminophenylboronic acid), metal chelate affinity chromatography (e.g. with Ni(II)- and Cu(II)-affinity material), size exclusion chromatography, and electrophoretical methods (such as gel electrophoresis, capillary electrophoresis) (Vijayalakshmi, M. A., Appl. Biochem. Biotech. 75 (1998) 93-102).

A first aspect as reported herein is a method for the preparation of an immunoglobulin solution comprising
    providing an immunoglobulin solution with a protein concentration of at least 100 g/l,
    filtering the immunoglobulin solution through a combination of a first and second filter unit, whereby the first filter unit comprises a pre-filter an a main-filter with a pore size of 3.0 μm and 0.8 μm, respectively, and the second filter unit comprises a pre-filter and a main-filter with a pore size of 0.45 μm and 0.22 μm, respectively, by applying the solution to the filter combination and by applying pressure and thereby preparing an immunoglobulin solution.

In one embodiment the protein concentration is of from 100 g/l to 300 g/l. In another embodiment the protein concentration is of from 100 g/l up to 200 g/l. In a further embodiment the protein concentration is of from 120 g/l to 165 g/l. In another embodiment the immunoglobulin solution has a volume of from 3 liter to 100 liter. This solution volume is equivalent to a total mass of the immunoglobulin of from 300 g to 50,000 g. In one embodiment the volume is of from 3.1 liter to 80 liter. At a protein concentration of from 120 g/l to 165 g/l this solution volume is equivalent to a total mass of the immunoglobulin of from 370 g to 13,200 g. In one embodiment the immunoglobulin is an anti-IL13 receptor alpha antibody. In another embodiment the immunoglobulin is an anti-HER2 antibody.

Another aspect as reported herein is a method for producing an immunoglobulin comprises the following steps
    cultivating a cell comprising a nucleic acid encoding the immunoglobulin,
    recovering the immunoglobulin from the cell or the cultivation medium,
    purifying the immunoglobulin with one or more chromatography steps, and providing a purified immunoglobulin solution, and
    filtrating the purified immunoglobulin solution through a combination of filters as reported herein, i.e. a combination of a first and second filter unit, whereby the first filter unit comprises a pre-filter with a pore size of 3.0 μm and a main-filter with a pore size of 0.8 μm, respectively, and the second filter unit comprises a pre-filter with a pore size of 0.45 μm and a main-filter with a pore size of 0.22 μm, respectively, by applying the solution to the filter combination and by applying pressure.

In one embodiment the cell is a prokaryotic cell or a eukaryotic cell. In one embodiment in which the cell is a prokaryotic cell the cell is selected from *E. coli* cells, or bacillus cells. In one embodiment in which the cell is a eukaryotic cell the cell is selected from mammalian cells, in a special embodiment from CHO cells, BHK cells, HEK cells, Per.C6® cells and hybridoma cells. In one embodiment the cell is a mammalian cell selected from CHO-K1 and CHO DG44. In one embodiment the cultivating is at a temperature of from 20° C. to 40° C., and for a period of from 4 to 28 days. In one embodiment the purifying is with a protein A affinity chromatography step and at least one step selected from cation exchange chromatography, anion exchange chromatography, and hydrophobic interaction chromatography.

It has been found that a combination of a first filter unit comprising a pre-filter an a main-filter with a pore size of 3.0 μm and 0.8 μm, respectively, and a second filter unit comprising a pre-filter and a main-filter with a pore size of 0.45 μm and 0.22 μm, respectively, is advantageous for processing (filtrating) highly concentrated immunoglobulin solution by allowing the filtration of a complete batch of a concentrated immunoglobulin solution without the need to replace the filter.

It has further been found that in the filter combination it is advantageous that each of the two filters employed in the units as well as the filter combination has approximately the same filter area, i.e. within two times the area of the smallest filter.

It has further been found that depending on the components of the solution beside the immunoglobulin different pressure and concentration ranges provide for advantageous processes.

If the solution is a concentrated immunoglobulin solution with a concentration of 160 g/l or more, i.e. 165 g/l or 170 g/l, to which no sugar or surfactant has been added then the method is operated in one embodiment with an applied pressure of 1.45 bar or more, in another of 1.5 bar or more. If the solution is a concentrated immunoglobulin solution with a concentration of 125 g/l or more, i.e. 130 g/l or 135 g/l, to which at least a sugar and a surfactant have been added then the method is operated in an embodiment with an applied pressure of 0.75 bar or less, in another embodiment of 0.7 bar or less.

Another aspect as reported herein is a kit comprising a first filter unit comprising a pre-filter and a main-filter with a pore size of 3.0 µm and 0.8 µm, respectively, and a second filter unit comprising a pre-filter and a main-filter with a pore size of 0.45 µm and 0.22 µm, respectively. Another aspect as reported herein is the use of a filter comprising a first filter unit comprising a pre-filter and a main-filter with a pore size of 3.0 µm and 0.8 µm, respectively, and a second filter unit comprising a pre-filter and a main-filter with a pore size of 0.45 µm and 0.22 µm, respectively for the filtration of a concentrated immunoglobulin solution with a protein concentration of at least 100 g/l.

The following examples and referenced figures are provided to aid the understanding of the present invention, the true scope of which is set forth in the appended claims. It is understood that modifications can be made in the procedures set forth without departing from the spirit of the invention.

Example 1

Material and Methods

Antibody

An exemplary antibody is an immunoglobulin against the IL13 receptor α1 protein (anti-IL13Rα1 antibody) e.g. as reported in SEQ ID NO: 01 to 12 of WO 2006/072564 (incorporated herein by reference).

Another exemplary immunoglobulin is an anti-HER2 antibody reported in WO 92/022653, WO 99/057134, WO 97/04801, U.S. Pat. Nos. 5,677,171 and 5,821,337 (incorporated herein by reference).

Filter

Herein among others a Sartobran P 0.45 µm+0.2 µm filter cartridge and a Sartoclean CA 3.0 µm+0.8 µm filter cartridge have been exemplarily employed. Both filter cartridges are available from Sartorius AG, Göttingen, Germany.

Analytical Methods

Size Exclusion Chromatography:
   resin: TSK 3000 (Tosohaas)
   column: 300×7.8 mm
   flow rate: 0.5 ml/min
   buffer: 200 mM potassium phosphate containing 250 mM potassium chloride, adjusted to pH 7.0
   wavelength: 280 nm DNA-threshold-system: see e.g. Merrick, H., and Hawlitschek, G., Biotech Forum Europe 9 (1992) 398-403

Protein A ELISA: The wells of a micro titer plate are coated with a polyclonal anti-protein A-IgG derived from chicken. After binding non-reacted antibody is removed by washing with sample buffer. For protein A binding a defined sample volume is added to the wells. The protein A present in the sample is bound by the chicken antibody and retained in the wells of the plate. After the incubation the sample solution is removed and the wells are washed. For detection are added subsequently a chicken derived polyclonal anti-protein A-IgG-biotin conjugate and a Streptavidin peroxidase conjugate. After a further washing step substrate solution is added resulting in the formation of a colored reaction product. The intensity of the color is proportional to the protein A content of the sample. After a defined time the reaction is stopped and the absorbance is measured.

Host cell protein (HCP) ELISA: The walls of the wells of a micro titer plate are coated with a mixture of serum albumin and Streptavidin. A goat derived polyclonal antibody against HCP is bound to the walls of the wells of the micro titer plate. After a washing step different wells of the micro titer plate are incubated with a HCP calibration sequence of different concentrations and sample solution. After the incubation not bound sample material is removed by washing with buffer solution. For the detection the wells are incubated with an antibody peroxidase conjugate to detect bound host cell protein. The fixed peroxidase activity is detected by incubation with ABTS and detection at 405 nm.

Example 2

Filtration of an Anti-HER2 Antibody with a Single Filter of 0.45 µm and 0.22 µm Pore Size In this example it is shown that a highly concentrated immunoglobulin solution cannot be filtered with a single sterile filter with a pore size of 0.45 µm (pre-filter) and 0.22 µm (main-filter) without blocking of the pores of the filter with a loading of more than 2,460 g protein per square meter of filter area.

In this example a single filter with a pore size of 0.45 µm and 0.22 µm and a total filter area of 0.2 square meters has been employed.

TABLE 1

Solutions employed in the single filter filtration.

| | solution No. | | | | |
|---|---|---|---|---|---|
| | 1 | 2 | 3 | 4 | 5 |
| protein mass [g] | 473 | 491 | 496 | 501 | 542 |
| volume [l] | 3.940 | 4.200 | 4.134 | 4.139 | 4.516 |
| loading [g/m$^2$] | 2,365 | 2,455 | 2,480 | 2,505 | 2,710 |

The concentrated immunoglobulin solutions were filtered through the single filter with the parameters as shown in Table 2.

TABLE 2

Process parameters.

| | solution No. | | | | |
|---|---|---|---|---|---|
| | 1 | 2 | 3 | 4 | 5 |
| volume flow [l/h] | 1.97 | 2.1 | Drop to 0 due to pore blocking | Drop to 0 due to pore blocking | Drop to 0 due to pore blocking |
| mass flow [g/h] | 237 | 246 | Drop to 0 due to pore blocking | Drop to 0 due to pore blocking | Drop to 0 due to pore blocking |

For solutions No. 3 to 5 the pores of the single filter were blocked prior to the complete filtration of the batch volume. To complete the filtration the blocked filter had to be changed resulting in additional time required and loss of product.

TABLE 3

Results of the filtration.

| | solution No. | | | | |
|---|---|---|---|---|---|
| | 1 | 2 | 3 | 4 | 5 |
| protein mass passing the filter [g/m$^2$] | 2,365 | 2,455 | 960 | 968 | 1,440 |
| volume passing the filter [l] | 3.940 | 4.200 | 1.600 | 1.600 | 2.400 |
| pore blocking of the filter | NO | NO | YES | YES | YES |

Example 3

Filtration of an Anti-HER2 Antibody with a Combination of a First Filter with a Pore Size of 3.0 μm and 0.8 μm and a Second Filter with a Pore Size of 0.45 μm and 0.22 μm In this example it is shown that a highly concentrated immunoglobulin solution can be filtered with a combination of two filters with a pore size of 3.0 μm (pre-filter) and 0.8 μm (main-filter) and of 0.45 μm (pre-filter) and 0.22 μm (main-filter) without blocking of the pores of the filter independent from the loading of protein per square meter of total filter area.

In this example a combined filter with a first filter unit with a pore size of 3.0 μm and 0.8 μm, respectively, and a second filter unit with a pore size of 0.45 μm and 0.22 μm, respectively, and a filter area each of 0.6 square meters has been employed.

TABLE 4

Solutions employed in the combined filter filtration.

| | solution No. | | | | |
|---|---|---|---|---|---|
| | 6 | 7 | 8 | 9 | 10 |
| protein mass [g] | 5,217 | 5,191 | 5,356 | 6,151 | 5,580 |
| volume [l] | 42.070 | 42.201 | 43.542 | 48.055 | 44.998 |
| loading [g/m$^2$] | 4,347.5 | 4,325.8 | 4,463.3 | 5,125.8 | 4,650.0 |

The concentrated immunoglobulin solutions were filtered through the combination of the two filters with the parameters as shown in Table 5.

TABLE 5

Process parameters.

| | solution No. | | | | |
|---|---|---|---|---|---|
| | 6 | 7 | 8 | 9 | 10 |
| volume flow [l/h] | 38.95 | 42.20 | 43.54 | 33.02 | 45.00 |
| mass flow [g/h] | 4830 | 5191 | 5356 | 4226 | 5580 |

For none of the solutions No. 6 to 10 the pores of the combined filters were blocked prior to the complete filtration of the batch volume.

TABLE 6

Results of the filtration.

| solution No. | 6 | 7 | 8 | 9 | 10 |
|---|---|---|---|---|---|
| protein mass passing the filter [g/m$^2$] | 4,347.5 | 4,325.8 | 4,463.3 | 5,125.8 | 4,650.0 |
| volume passing the filter [l] | 42.070 | 42.201 | 43.542 | 48.055 | 44.998 |
| pore blocking of the filter | NO | NO | NO | NO | NO |

Example 4

Filtration of an Anti-IL13Rα Antibody with a Filter Combination of a Filter with 3.0 μm and 0.8 μm Pore Size and a Filter with 0.45 μm and 0.22 μm Pore Size and Both Filters with Different Filter Areas In this example it is shown that a conditioned protein A eluate can be filtered with a combination of two filters but the flow has to be reduced if the filter area does not match between the two filters.

In this example a filter unit with a pore size of 3.0 μm (pre-filter) and 0.8 μm (main-filter) with a filter area of 1.8 square meters and a filter unit with a pore size of 0.45 μm (pre-filter) and 0.22 μm (main-filter) with a filter area of 0.6 square meters has been employed.

TABLE 7

Solutions employed in the combined filter filtration.

| solution No. | 11 | 12 | 13 | 14 | 15 |
|---|---|---|---|---|---|
| protein mass [g] | 1,169.0 | 1,299.6 | 1,154.4 | 1,220.4 | 1,284.7 |
| volume [l] | 71.4 | 76.0 | 74.0 | 67.8 | 70.2 |
| loading [g/m$^2$] | 487.1 | 541.5 | 481.0 | 508.5 | 535.3 |

The concentrated immunoglobulin solutions were filtered through the combined filter with the parameters as shown in Table 8.

TABLE 8

Process parameters.

| solution No. | 11 | 12 | 13 | 14 | 15 |
|---|---|---|---|---|---|
| volume flow [l/h] | Drop to 0 due to pore blocking | 22 | 13 | 12 | 98 |
| mass flow [g/h] | Drop to 0 due to pore blocking | 376 | 203 | 216 | 1793 |

For solution No. 11 the pores of the combined filter were blocked prior to the complete filtration of the batch volume. To complete the filtration the blocked filter had to be changed resulting in additional time required and loss of product.

TABLE 9

Results of the filtration.

| solution No. | 1 | 2 | 3 | 4 | 5 |
|---|---|---|---|---|---|
| protein mass passing the filter [g/m$^2$] | 347.9 | 541.5 | 481.0 | 508.5 | 535.3 |
| volume passing the filter [l] | 51.0 | 76.0 | 74.0 | 67.8 | 70.2 |
| pore blocking of the filter | YES | NO | NO | NO | NO |

In order to prevent filter blocking as in the experiment with solution No. 11 the flow through the membrane had to be reduced in experiments with solutions No. 12 to 14. In experiment with solution No. 15 the protein A eluate has been decanted resulting in a loss of protein.

Example 5

Filtration of an Anti-IL13Rα Antibody with a Filter Combination of a Filter with 3.0 μm and 0.8 μm Pore Size and a Filter with 0.45 μm and 0.22 μm Pore Size and Both Filters Each with the Same Filter Area In this example it is shown that a conditioned protein A eluate can be filtered with a combination of two filters without a reduction of the flow if the filter area does match between the two filters.

In this example the filter unit with a pore size of 3.0 μm and 0.8 μm has a filter area of 0.2 square meters and the filter unit with a pore size of 0.45 μm and 0.22 μm has a filter area of 0.2 square meters.

TABLE 10

Solutions employed in the combined filter filtration.

| solution No. | 16 | 17 | 18 | 19 | 20 |
|---|---|---|---|---|---|
| protein mass [g] | 495 | 634 | 825 | 861 | 956 |
| volume [l] | 3.5 | 4.14 | 5.5 | 5.6 | 6.3 |
| loading [g/m$^2$] | 1,237.5 | 1,585.0 | 2,062.5 | 2,152.5 | 2,390 |

For none of the solutions No. 16 to 20 the pores of the combined filters were blocked prior to the complete filtration of the batch volume.

TABLE 11

Results of the filtration.

| solution No. | 16 | 17 | 18 | 19 | 20 |
|---|---|---|---|---|---|
| Protein mass passing the filter [g/m$^2$] | 1,237.5 | 1,585.0 | 2,062.5 | 2,152.5 | 2,390 |
| Volume passing the filter [l] | 3.5 | 4.14 | 5.5 | 5.6 | 6.3 |
| Pore blocking of the filter | NO | NO | NO | NO | NO |

Example 6

Filtration of Different Antibody Solutions with Different Filter Combinations with Different Protein Concentrations, Different Compounds in Solution and Different Applied Pressures Solutions comprising either an anti-IL13Rα antibody or an anti-HER2 antibody were filtered with a filter combination employing different filter area and filter pore size as well as different excipients and applied pressure.

The used filter combinations are listed in Table 12. In the following the denotation 'A1', 'A2', 'B1', and 'B2' will be used therefore.

TABLE 12

Filter combinations

| combination | filter 1 pore size/ diameter | filter 2 pore size/ diameter | filter 3 pore size/ diameter | filter 4 pore size/ diameter |
|---|---|---|---|---|
| A1 | 1.2 μm/26 mm | 0.8 μm/26 mm | 0.45 μm/26 mm | 0.2 μm/26 mm |
| A2 | 1.2 μm/47 mm | 0.8 μm/26 mm | 0.45 μm/26 mm | 0.2 μm/26 mm |
| B1 | 3.0 μm/26 mm | 0.8 μm/26 mm | 0.45 μm/26 mm | 0.2 μm/26 mm |
| B2 | 3.0 μm/47 mm | 0.8 μm/26 mm | 0.45 μm/26 mm | 0.2 μm/26 mm |

In the following Tables 13 to 20 and in corresponding FIGS. 1 to 8 the results obtained with different filter combinations, different antibody solutions and different filtering conditions are presented.

TABLE 13

Figure 1:
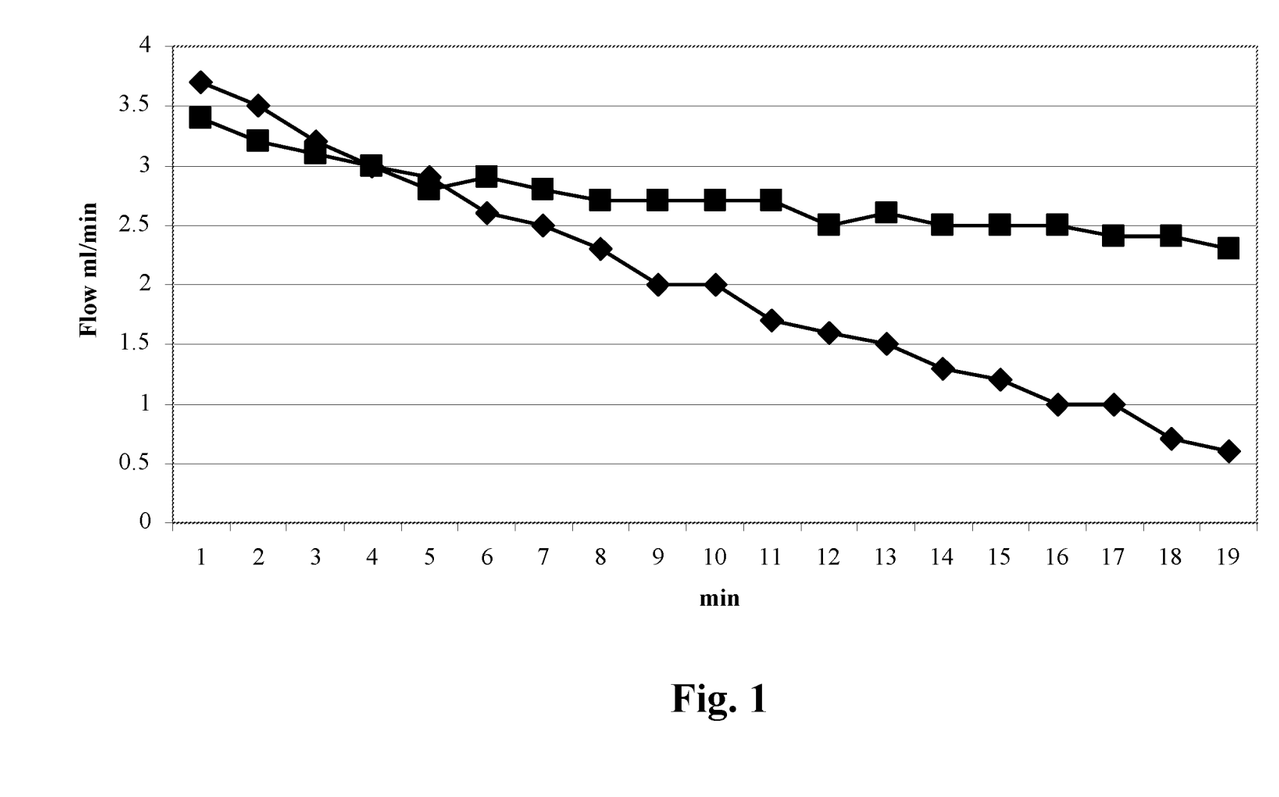
FIG. 1 shows time course of permeate flow obtained with an anti-HER2 antibody solution with an antibody concentration of 222 mg/ml and an applied pressure of 2.0 bar (diamonds=1.2 μm pore size filter containing combination; squares=3.0 μm pore size filter containing combination).

Results obtained with an anti-HER2 antibody solution with an antibody concentration of 222 mg/ml and an applied pressure of 2.0 bar.

| combination | filtration duration [min] | flow [ml/min] | Combination | filtration duration [min] | flow [ml/min] |
|---|---|---|---|---|---|
| A1 | 1 | 3.7 | B1 | 1 | 3.4 |
|  | 2 | 3.5 |  | 2 | 3.2 |
|  | 3 | 3.2 |  | 3 | 3.1 |
|  | 4 | 3.0 |  | 4 | 3.0 |
|  | 5 | 2.9 |  | 5 | 2.8 |
|  | 6 | 2.6 |  | 6 | 2.9 |
|  | 7 | 2.5 |  | 7 | 2.8 |
|  | 8 | 2.3 |  | 8 | 2.7 |
|  | 9 | 2.0 |  | 9 | 2.7 |
|  | 10 | 2.0 |  | 10 | 2.7 |
|  | 11 | 1.7 |  | 11 | 2.7 |
|  | 12 | 1.6 |  | 12 | 2.5 |
|  | 13 | 1.5 |  | 13 | 2.6 |
|  | 14 | 1.3 |  | 14 | 2.5 |
|  | 15 | 1.2 |  | 15 | 2.5 |

TABLE 14

Figure 2:
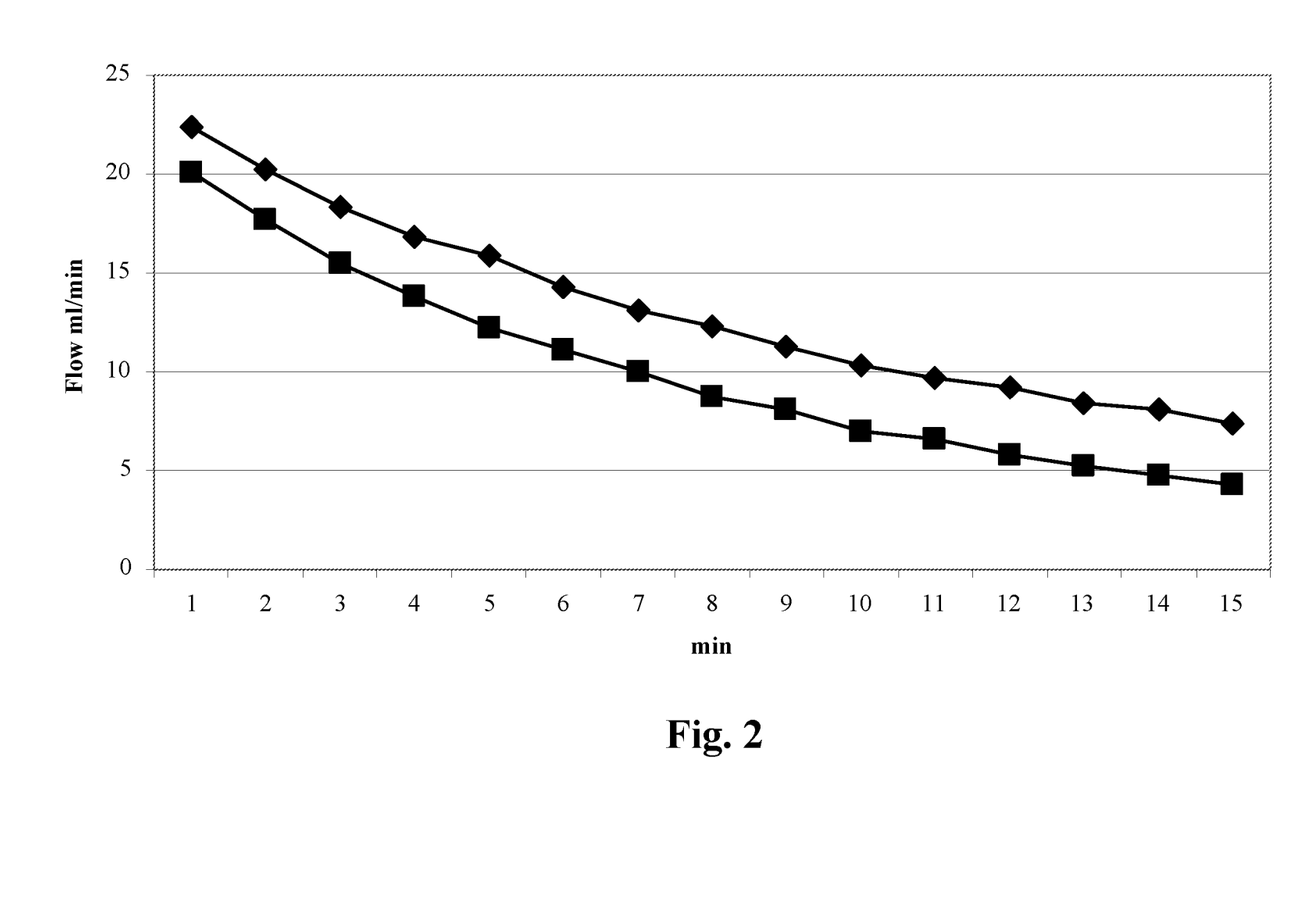
FIG. 2 shows time course of permeate flow obtained with an anti-HER2 antibody solution with an antibody concentration of 125 mg/ml supplemented with about 200 mM trehalose and about 0.05% (w/v) Tween 20 and an applied pressure of 2.0 bar (diamonds=1.2 μm pore size filter containing combination; squares=3.0 μm pore size filter containing combination).

Results obtained with an anti-HER2 antibody solution with an antibody concentration of 125 mg/ml supplemented with about 200 mM trehalose and about 0.05% (w/v) Tween 20 and an applied pressure of 2.0 bar.

| combination | filtration duration [min] | flow [ml/min] | Combination | filtration duration [min] | flow [ml/min] |
|---|---|---|---|---|---|
| A1 | 1 | 22.4 | B1 | 1 | 20.1 |
|  | 2 | 20.2 |  | 2 | 17.7 |
|  | 3 | 18.3 |  | 3 | 15.5 |
|  | 4 | 16.8 |  | 4 | 13.8 |
|  | 5 | 15.9 |  | 5 | 12.2 |
|  | 6 | 14.3 |  | 6 | 11.1 |
|  | 7 | 13.1 |  | 7 | 10.0 |
|  | 8 | 12.3 |  | 8 | 8.7 |
|  | 9 | 11.3 |  | 9 | 8.1 |
|  | 10 | 10.3 |  | 10 | 7.0 |
|  | 11 | 9.7 |  | 11 | 6.6 |
|  | 12 | 9.2 |  | 12 | 5.8 |
|  | 13 | 8.4 |  | 13 | 5.2 |
|  | 14 | 8.1 |  | 14 | 4.8 |
|  | 15 | 7.4 |  | 15 | 4.3 |

TABLE 15

Figure 3:
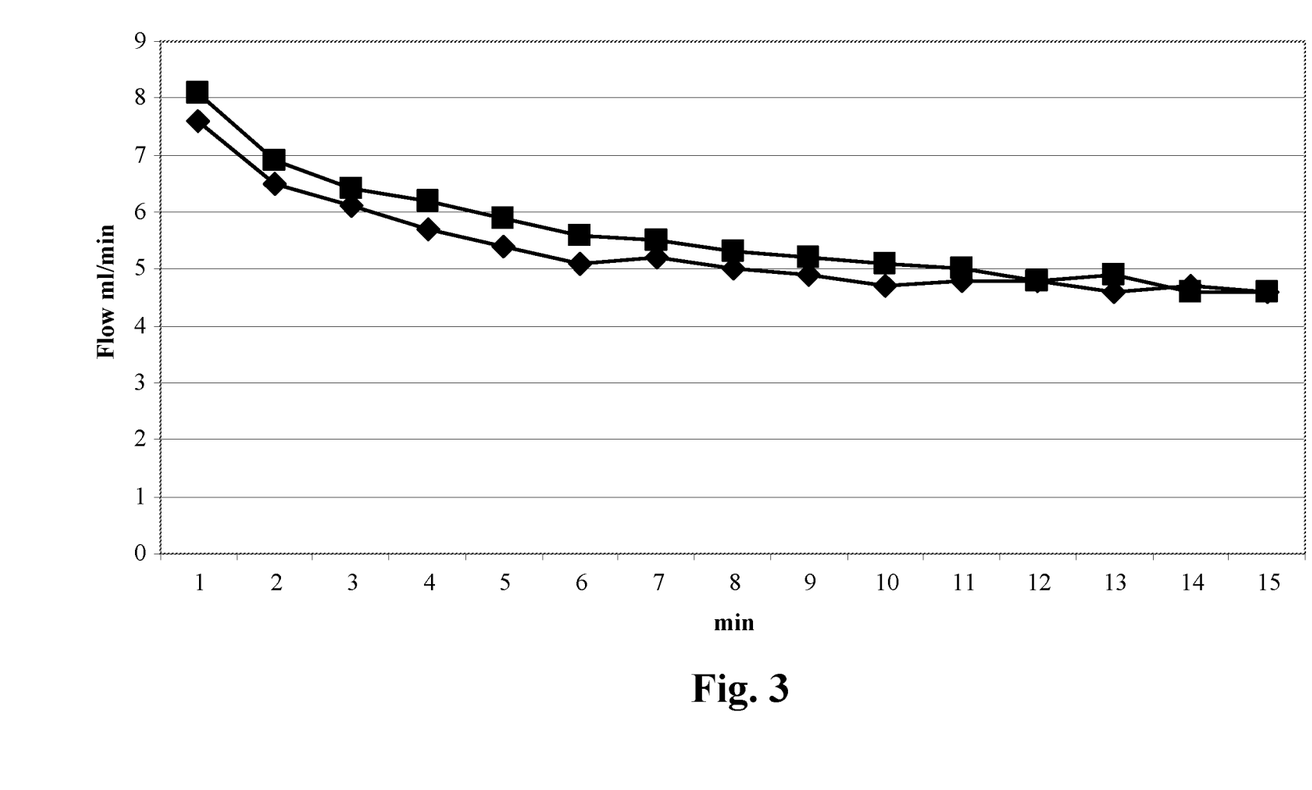
FIG. 3 shows time course of permeate flow obtained with an anti-HER2 antibody solution with an antibody concentration of 162 mg/ml and an applied pressure of 1.8 bar (diamonds=1.2 μm pore size filter containing combination; squares=3.0 μm pore size filter containing combination).

Results obtained with an anti-HER2 antibody solution with an antibody concentration of 162 mg/ml and an applied pressure of 1.8 bar.

| combination | filtration duration [min] | flow [ml/min] | Combination | filtration duration [min] | flow [ml/min] |
|---|---|---|---|---|---|
| A2 | 1 | 7.6 | B2 | 1 | 8.1 |
|  | 2 | 6.5 |  | 2 | 6.9 |
|  | 3 | 6.1 |  | 3 | 6.4 |
|  | 4 | 5.7 |  | 4 | 6.2 |
|  | 5 | 5.4 |  | 5 | 5.9 |
|  | 6 | 5.1 |  | 6 | 5.6 |
|  | 7 | 5.2 |  | 7 | 5.5 |
|  | 8 | 5.0 |  | 8 | 5.3 |
|  | 9 | 4.9 |  | 9 | 5.2 |
|  | 10 | 4.7 |  | 10 | 5.1 |
|  | 11 | 4.8 |  | 11 | 5.0 |
|  | 12 | 4.8 |  | 12 | 4.8 |
|  | 13 | 4.6 |  | 13 | 4.9 |
|  | 14 | 4.7 |  | 14 | 4.6 |
|  | 15 | 4.6 |  | 15 | 4.6 |

TABLE 16

Figure 4:
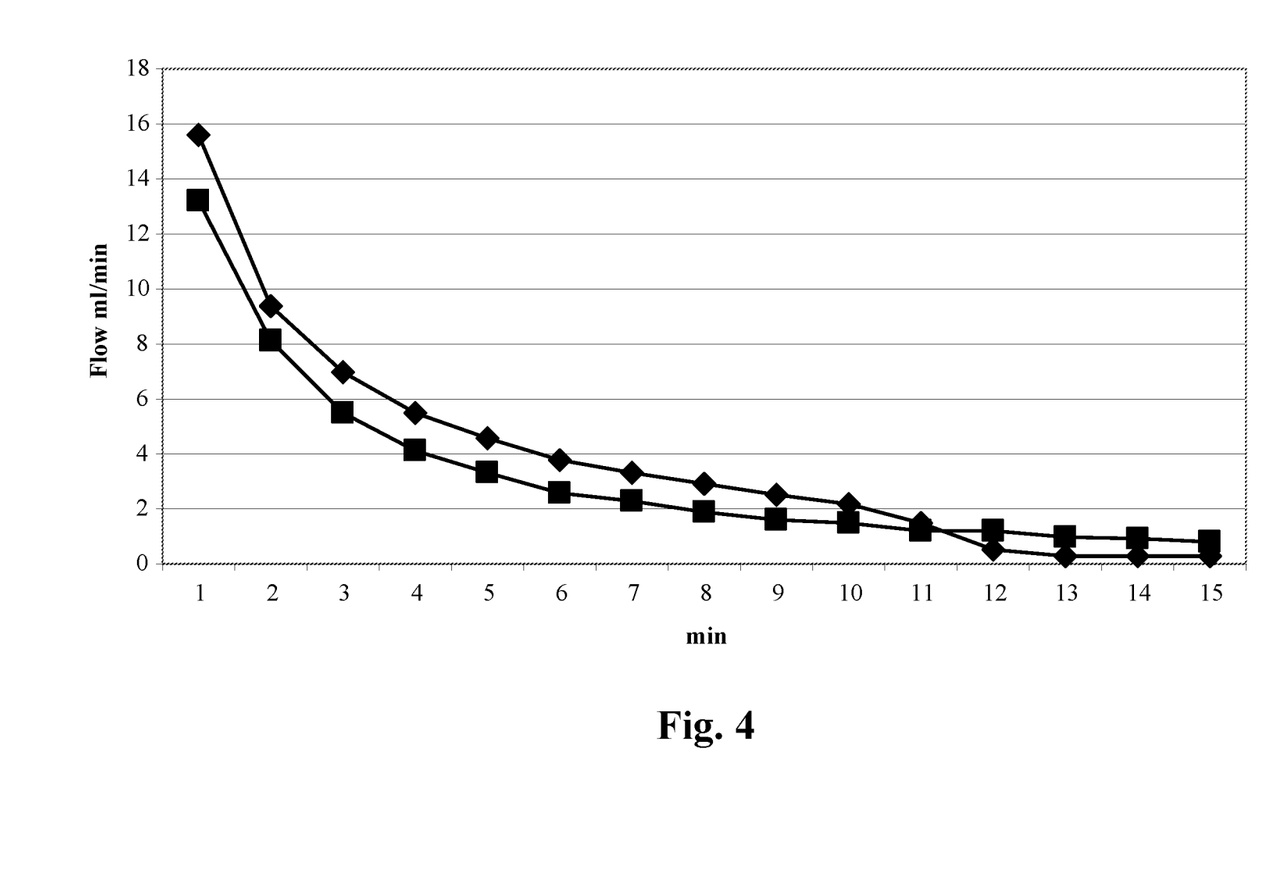
FIG. 4 shows time course of permeate flow obtained with an anti-IL13Rα antibody solution with an antibody concentration of 141 mg/ml supplemented with about 200 mM trehalose and about 0.2% (w/v) Poloxamer and an applied pressure of 1.6 bar (diamonds=1.2 μm pore size filter containing combination; squares=3.0 μm pore size filter containing combination).

Results obtained with an anti-IL13Rα antibody solution with an antibody concentration of 141 mg/ml supplemented with about 200 mM trehalose and about 0.2% (w/v) Poloxamer and an applied pressure of 1.6 bar.

| combination | filtration duration [min] | flow [ml/min] | Combination | filtration duration [min] | flow [ml/min] |
|---|---|---|---|---|---|
| A2 | 1 | 15.6 | B2 | 1 | 13.2 |
|  | 2 | 9.4 |  | 2 | 8.1 |
|  | 3 | 7.0 |  | 3 | 5.5 |
|  | 4 | 5.5 |  | 4 | 4.1 |
|  | 5 | 4.6 |  | 5 | 3.3 |
|  | 6 | 3.8 |  | 6 | 2.6 |
|  | 7 | 3.3 |  | 7 | 2.3 |
|  | 8 | 2.9 |  | 8 | 1.9 |
|  | 9 | 2.5 |  | 9 | 1.6 |
|  | 10 | 2.2 |  | 10 | 1.5 |
|  | 11 | 1.5 |  | 11 | 1.2 |
|  | 12 | 0.5 |  | 12 | 1.2 |
|  | 13 | 0.3 |  | 13 | 1.0 |
|  | 14 | 0.3 |  | 14 | 0.9 |
|  | 15 | 0.3 |  | 15 | 0.8 |

TABLE 17

Figure 5:
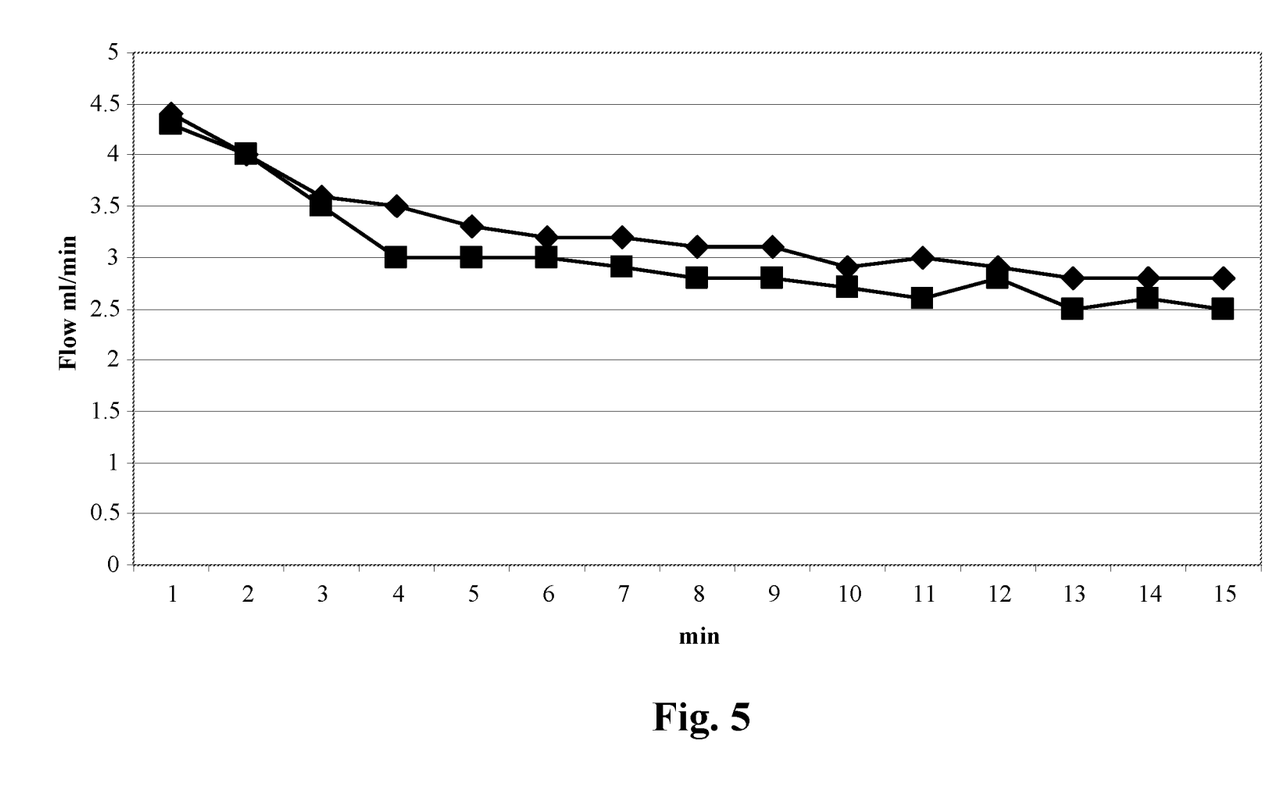
FIG. 5 shows time course of permeate flow obtained with an anti-HER2 antibody solution with an antibody concentration of 162 mg/ml and an applied pressure of 1.1 bar (diamonds=1.2 μm pore size filter containing combination; squares=3.0 μm pore size filter containing combination).

Results obtained with an anti-HER2 antibody solution with an antibody concentration of 162 mg/ml and an applied pressure of 1.1 bar.

| combination | filtration duration [min] | flow [ml/min] | Combination | filtration duration [min] | flow [ml/min] |
|---|---|---|---|---|---|
| A1 | 1 | 4.4 | B1 | 1 | 4.3 |
|  | 2 | 4.0 |  | 2 | 4.0 |
|  | 3 | 3.6 |  | 3 | 3.5 |
|  | 4 | 3.5 |  | 4 | 3.0 |
|  | 5 | 3.3 |  | 5 | 3.0 |
|  | 6 | 3.2 |  | 6 | 3.0 |
|  | 7 | 3.2 |  | 7 | 2.9 |
|  | 8 | 3.1 |  | 8 | 2.8 |
|  | 9 | 3.1 |  | 9 | 2.8 |
|  | 10 | 2.9 |  | 10 | 2.7 |
|  | 11 | 3.0 |  | 11 | 2.6 |
|  | 12 | 2.9 |  | 12 | 2.8 |
|  | 13 | 2.8 |  | 13 | 2.5 |
|  | 14 | 2.8 |  | 14 | 2.6 |
|  | 15 | 2.8 |  | 15 | 2.5 |

TABLE 18

Figure 6:
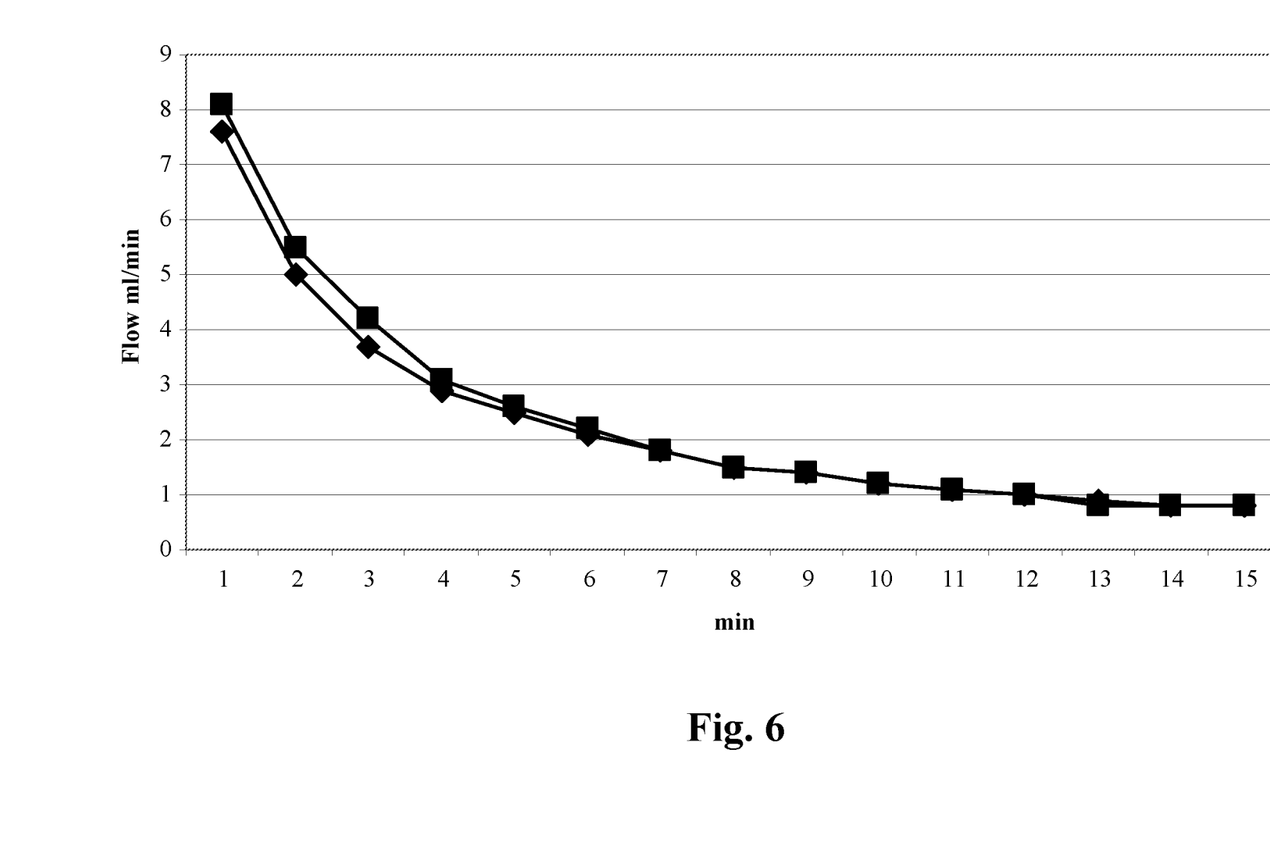
FIG. 6 shows time course of permeate flow obtained with an anti-IL13Rα antibody solution with an antibody concentration of 141 mg/ml supplemented with trehalose and Poloxamer and an applied pressure of 0.8 bar (diamonds=1.2 μm pore size filter containing combination; squares=3.0 μm pore size filter containing combination).

Results obtained with an anti-IL13Rα antibody solution with an antibody concentration of 141 mg/ml supplemented with trehalose and Poloxamer and an applied pressure of 0.8 bar.

| combination | filtration duration [min] | flow [ml/min] | Combination | filtration duration [min] | flow [ml/min] |
|---|---|---|---|---|---|
| A2 | 1 | 7.6 | B2 | 1 | 8.1 |
|  | 2 | 5.0 |  | 2 | 5.5 |
|  | 3 | 3.7 |  | 3 | 4.2 |
|  | 4 | 2.9 |  | 4 | 3.1 |
|  | 5 | 2.5 |  | 5 | 2.6 |
|  | 6 | 2.1 |  | 6 | 2.2 |
|  | 7 | 1.8 |  | 7 | 1.8 |
|  | 8 | 1.5 |  | 8 | 1.5 |
|  | 9 | 1.4 |  | 9 | 1.4 |
|  | 10 | 1.2 |  | 10 | 1.2 |
|  | 11 | 1.1 |  | 11 | 1.1 |
|  | 12 | 1.0 |  | 12 | 1.0 |
|  | 13 | 0.9 |  | 13 | 0.8 |
|  | 14 | 0.8 |  | 14 | 0.8 |
|  | 15 | 0.8 |  | 15 | 0.8 |

TABLE 19

Figure 7:
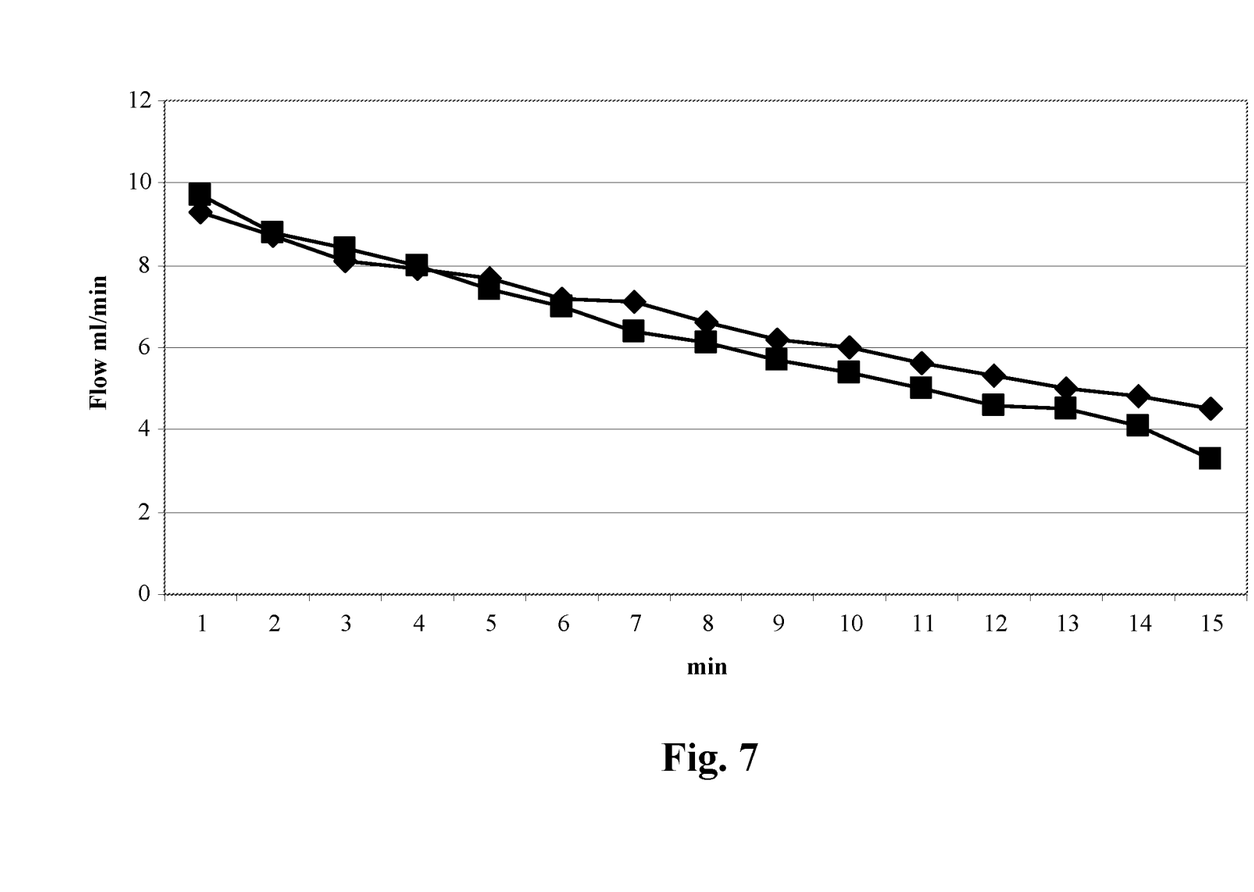
FIG. 7 shows time course of permeate flow obtained with an anti-HER2 antibody solution with an antibody concentration of 125 mg/ml supplemented with trehalose and Tween 20 and an applied pressure of 0.8 bar (diamonds=1.2 μm pore size filter containing combination; squares=3.0 μm pore size filter containing combination).

Results obtained with an anti-HER2 antibody solution with an antibody concentration of 125 mg/ml supplemented with trehalose and Tween 20 and an applied pressure of 0.8 bar.

| combination | filtration duration [min] | flow [ml/min] | Combination | filtration duration [min] | flow [ml/min] |
|---|---|---|---|---|---|
| A1 | 1 | 9.3 | B1 | 1 | 9.7 |
|  | 2 | 8.7 |  | 2 | 8.8 |
|  | 3 | 8.1 |  | 3 | 8.4 |
|  | 4 | 7.9 |  | 4 | 8.0 |
|  | 5 | 7.7 |  | 5 | 7.4 |
|  | 6 | 7.2 |  | 6 | 7.0 |
|  | 7 | 7.1 |  | 7 | 6.4 |
|  | 8 | 6.6 |  | 8 | 6.1 |
|  | 9 | 6.2 |  | 9 | 5.7 |
|  | 10 | 6.0 |  | 10 | 5.4 |
|  | 11 | 5.6 |  | 11 | 5.0 |
|  | 12 | 5.3 |  | 12 | 4.6 |
|  | 13 | 5.0 |  | 13 | 4.5 |
|  | 14 | 4.8 |  | 14 | 4.1 |
|  | 15 | 4.5 |  | 15 | 3.3 |

TABLE 20

Figure 8:
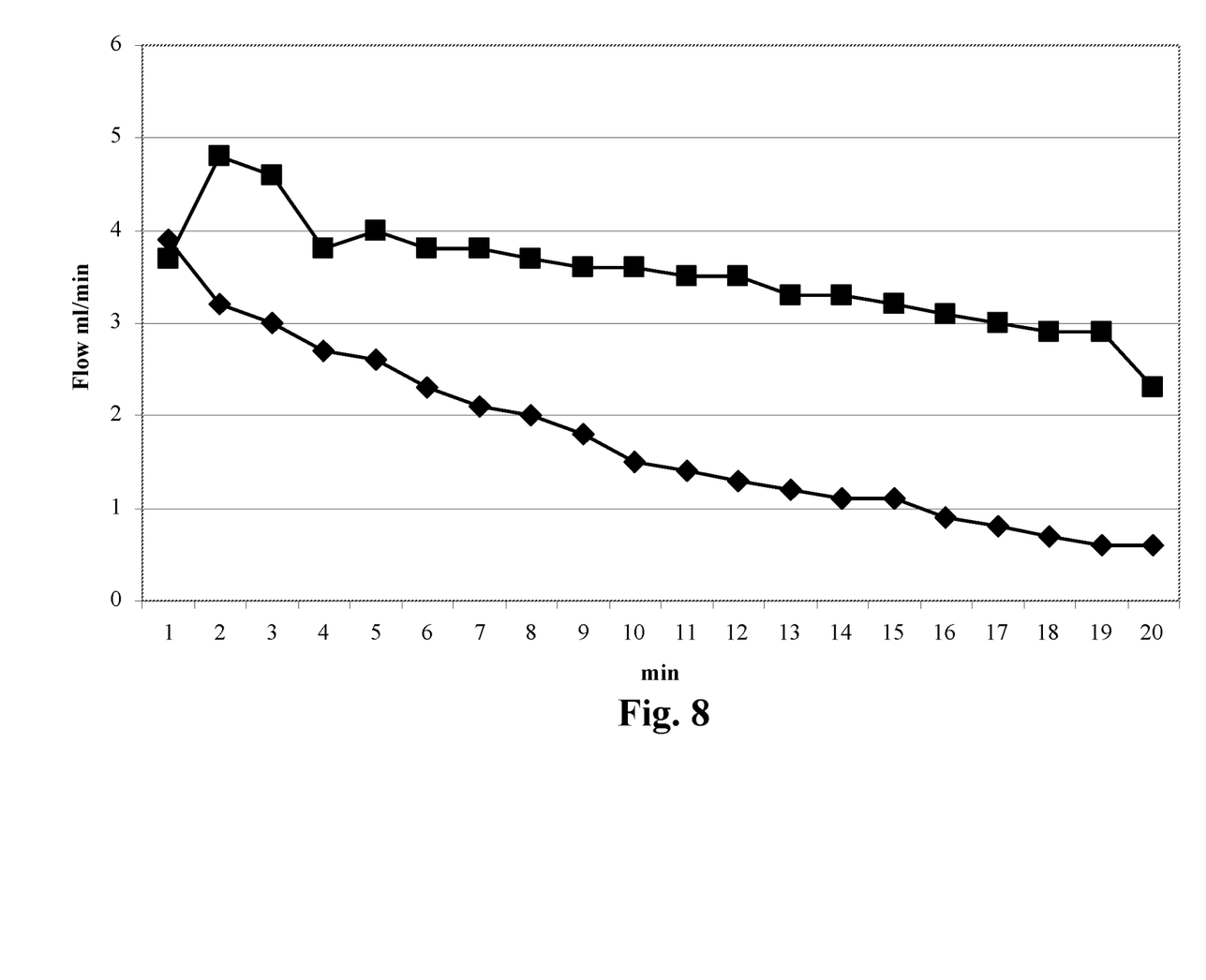
FIG. 8 shows time course of permeate flow obtained with an anti-HER2 antibody solution with an antibody concentration of 125 mg/ml supplemented with trehalose and Tween 20 and an applied pressure of 0.3 bar (diamonds=1.2 μm pore size filter containing combination; squares=3.0 μm pore size filter containing combination).

Results obtained with an anti-HER2 antibody solution with an antibody concentration of 125 mg/ml supplemented with trehalose and Tween 20 and an applied pressure of 0.3 bar.

| combination | filtration duration [min] | flow [ml/min] | Combination | filtration duration [min] | flow [ml/min] |
|---|---|---|---|---|---|
| A1 | 1 | 3.9 | B1 | 1 | 3.7 |
|  | 2 | 3.2 |  | 2 | 4.8 |
|  | 3 | 3.0 |  | 3 | 4.6 |
|  | 4 | 2.7 |  | 4 | 3.8 |
|  | 5 | 2.6 |  | 5 | 4.0 |
|  | 6 | 2.3 |  | 6 | 3.8 |
|  | 7 | 2.1 |  | 7 | 3.8 |
|  | 8 | 2.0 |  | 8 | 3.7 |
|  | 9 | 1.8 |  | 9 | 3.6 |
|  | 10 | 1.5 |  | 10 | 3.6 |
|  | 11 | 1.4 |  | 11 | 3.5 |
|  | 12 | 1.3 |  | 12 | 3.5 |
|  | 13 | 1.2 |  | 13 | 3.3 |
|  | 14 | 1.1 |  | 14 | 3.3 |
|  | 15 | 1.1 |  | 15 | 3.2 |

What is claimed is:

1. A method for producing an immunoglobulin solution comprising
   a) providing an immunoglobulin solution with a concentration of at least 100 g/l, and
   b) applying the immunoglobulin solution to a combination of a first and second filter unit, whereby the first filter unit comprises a pre-filter with a pore size of 3.0 µm and a main-filter with a pore size of 0.8 µm and the second filter unit comprises a pre-filter with a pore size of 0.45 µm and a main-filter with a pore size of 0.22 µm with a pressure of from 0.1 to 4.0 bar, and thereby producing an immunoglobulin solution.

2. A method for producing an immunoglobulin comprising the following steps
   a) cultivating a cell comprising a nucleic acid encoding an immunoglobulin,
   b) recovering the immunoglobulin from the cell or the cultivation medium,
   c) purifying the immunoglobulin with one or more chromatography steps, and providing an immunoglobulin solution,
   d) optionally adding a sugar, an amino acid and/or a detergent to the solution,
   e) concentrating the immunoglobulin solution to a concentration of 100 g/l or more with a method selected from diafiltration or tangential-flow filtration, and
   f) applying the immunoglobulin solution of the previous step to a combination of a first and second filter unit, whereby the first filter unit comprises a pre-filter with a pore size of 3.0 µm and a main-filter with a pore size of 0.8 µm and the second filter unit comprises a pre-filter with a pore size of 0.45 µm and a main-filter with a pore size of 0.22 µm with a pressure of from 0.1 to 4.0 bar, and thereby producing an immunoglobulin.

3. The method of claim 1 wherein the filter in the first and second filter unit have about the same filter area.

4. The method of claim 1 wherein the immunoglobulin solution has a concentration of from 100 g/l to 300 g/l.

5. The method of claim 1 wherein the immunoglobulin solution has a volume of from 3 liter to 100 liter.

6. The method of claim 1 wherein the immunoglobulin is an anti-IL13 receptor alpha antibody or an anti-HER2 antibody.

7. The method of claim 1 wherein the producing includes protein A affinity chromatography step and at least one step selected from cation exchange chromatography, anion exchange chromatography, and hydrophobic interaction chromatography.

8. The method of claim 1 wherein the immunoglobulin solution has a concentration of 160 g/l or more and the applying to the combination of filters is by applying a pressure of 1.45 bar or more.

9. The method of claim 1 wherein the immunoglobulin solution comprises a sugar and a surfactant and has a concentration of 125 mg/ml or more and the applying to the combination of the filter is by applying a pressure of 0.75 bar or less.

10. The method of claim 2 wherein the filter in the first and second filter unit have about the same filter area.

11. The method of claim 2 wherein the immunoglobulin solution has a concentration of from 100 g/l to 300 g/l.

12. The method of claim 2 wherein the immunoglobulin solution has a volume of from 3 liter to 100 liter.

13. The method of claim 2 wherein the immunoglobulin is an anti-IL13 receptor alpha antibody or an anti-HER2 antibody.

14. The method of claim 2 wherein the purifying is with a protein A affinity chromatography step and at least one step selected from cation exchange chromatography, anion exchange chromatography, and hydrophobic interaction chromatography.

15. The method of claim 2 wherein the immunoglobulin solution has a concentration of 160 g/l or more and the applying to the combination of filters is by applying a pressure of 1.45 bar or more.

16. The method of claim 2 wherein the immunoglobulin solution comprises a sugar and a surfactant and has a concentration of 125 mg/ml or more and the applying to the combination of the filter is by applying a pressure of 0.75 bar or less.

* * * * *